(12) United States Patent
Salzman

(10) Patent No.: US 8,535,275 B2
(45) Date of Patent: Sep. 17, 2013

(54) SYRINGE-ATTACHED TOPICAL ANESTHETIC DISPENSER

(75) Inventor: Marc J. Salzman, Louisville, KY (US)

(73) Assignee: BellaNovus Development Company LLC

( * ) Notice: Subject to any disclaimer, the term of this patent is extended or adjusted under 35 U.S.C. 154(b) by 962 days.

(21) Appl. No.: 12/213,892

(22) Filed: Jun. 26, 2008

(65) Prior Publication Data
US 2009/0326478 A1    Dec. 31, 2009

(51) Int. Cl.
*A61M 5/00* (2006.01)
*A61M 5/315* (2006.01)
*A61M 35/00* (2006.01)

(52) U.S. Cl.
USPC ........... 604/191; 604/112; 604/181; 604/187; 604/218; 604/236; 604/289; 604/310; 604/311

(58) Field of Classification Search
USPC .................. 604/112, 181, 187, 191, 218, 232, 604/236, 289, 310, 311, 173, 257, 258
See application file for complete search history.

(56) References Cited

U.S. PATENT DOCUMENTS

| | | | | |
|---|---|---|---|---|
| 3,605,742 | A | * | 9/1971 | Tibbs ............................ 604/112 |
| 4,725,265 | A | * | 2/1988 | Sairenji ......................... 604/112 |
| 5,236,419 | A | | 8/1993 | Seney |
| 5,341,993 | A | * | 8/1994 | Haber et al. ................... 239/331 |
| 6,312,412 | B1 | * | 11/2001 | Saied et al. ................... 604/191 |
| 6,565,538 | B2 | * | 5/2003 | Quinn et al. .................. 604/181 |
| 6,598,765 | B2 | * | 7/2003 | Pagel et al. ................... 222/214 |
| 6,936,028 | B2 | | 8/2005 | Hommann et al. |
| 2005/0245881 | A1 | * | 11/2005 | Meyer et al. .................. 604/232 |

OTHER PUBLICATIONS

Cassidy et al, A randomized double-blind, placebo-controlled trial of the EMLA patch for the reduction of pain associated with intramuscular injection in four to six-year-old children, Nov. 2001, Acta Paediatr, 90 (11), 1329-36.*
Buhse, Efficacy of EMLA Cream to Reduce Fear and Pain Associated with Interferon Beta-1 a Injection in Patients with Multiple Sclerosis, Aug. 2006, Journal of Neuroscience Nursing, 38.4, 222-6.*
Kundu et al, Principles of office anesthesia: part II. Topical anesthesia, Jul. 2002, Am Faro Physician, 66(1), 99-102.*
Himelstein et al, Topical application of lidocaine-prilocaine (EMLA) cream reduces the pain of intramuscular infiltration of saline solution, Nov. 1996, J Pediatr, 129 (5), 718-21.*

* cited by examiner

*Primary Examiner* — Kevin C Sirmons
*Assistant Examiner* — Shefali Patel
(74) *Attorney, Agent, or Firm* — H. Jay Spiegel

(57) ABSTRACT

A topical anesthetic dispenser is releasably attachable to a pre-filled disposable syringe. A clip receives a barrel of the syringe. The clip includes a receptacle portion receiving a pre-filled cannister of a topical numbing agent, wherein the cannister includes a generally cylindrical chamber portion receivable within the receptacle portion of the clip and a distal neck portion having an outlet allowing contents of the cannister to be dispensed. A dispenser attached to the distal neck portion of the cannister includes an elongated flexible tube surrounded by a rigid tube for at least a portion of a length of the elongated flexible tube. A pivotable lever carries a tube compressor including a pinching member extending through an opening in the rigid tube and spring biased to a position at which the pinching member pinches closed an elongated passageway through the flexible tube. The pivotable lever is spring biased to the position at which the flexible tube is pinched closed and is pivoted against the spring bias to open the flexible tube and dispense the numbing agent.

20 Claims, 2 Drawing Sheets

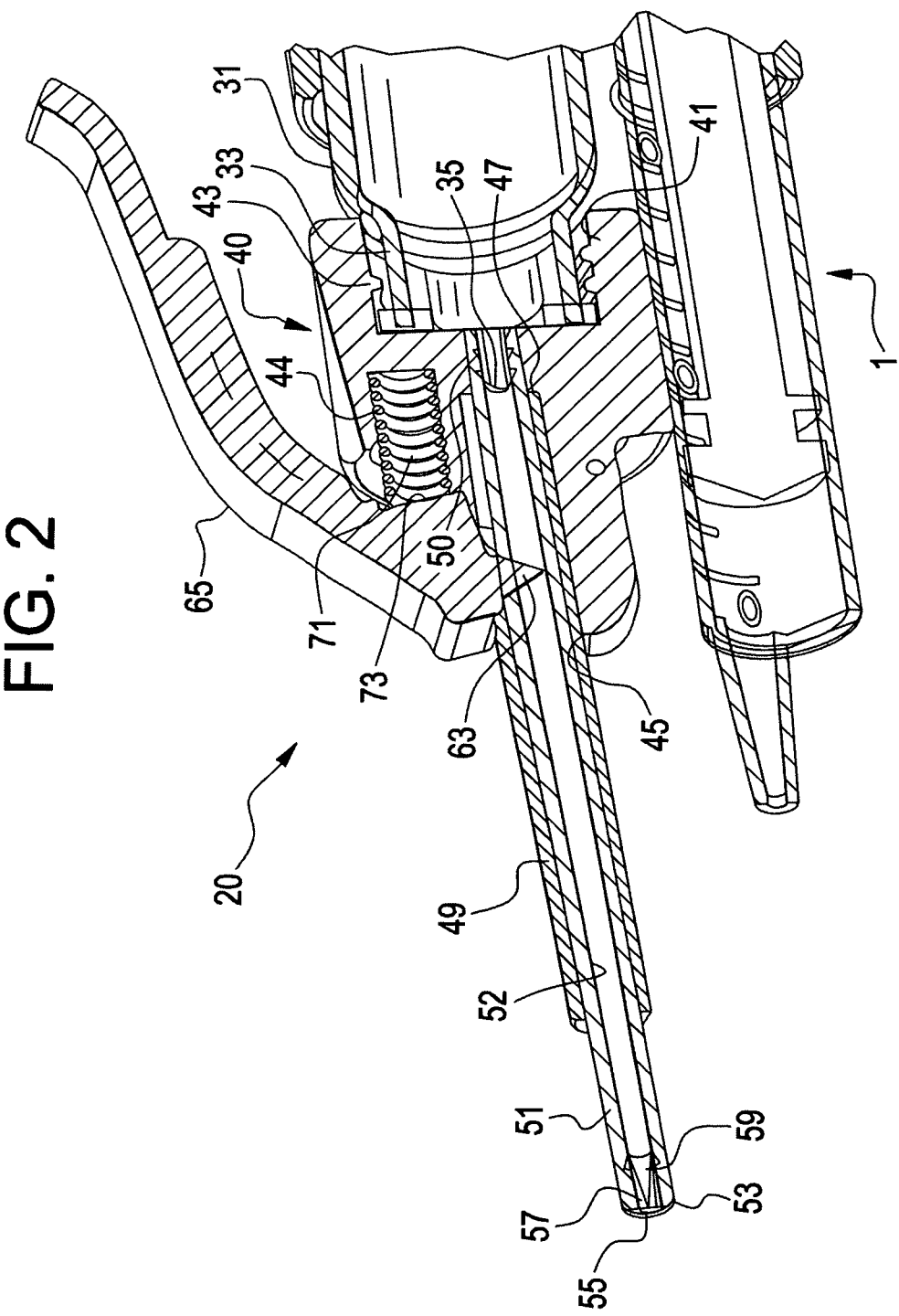

SYRINGE-ATTACHED TOPICAL ANESTHETIC DISPENSER

BACKGROUND OF THE INVENTION

The present invention relates to a syringe-attached topical anesthetic dispenser. Syringes are employed millions of times daily all over the world to inject medicines into people as well as animals. Many times, injections are made in areas of the body that are somewhat less sensitive to pain. Other locations of the body where injections are contemplated are significantly more sensitive to pain and the patient feels a pinching sensation that may be quite painful as the syringe needle is inserted beneath the skin. Such areas include, for example, areas of the face such as the forehead as well as the lips.

Use of cosmetic injections into the face of a patient has become more and more common. Thus, for example, a chemical known by the Trademark Botox® is often injected into the face, particularly into a patient's forehead, to paralyze the subcutaneous muscles and temporarily eliminate visible wrinkles in the forehead. Such injections typically last several months at most and must be repeated over and over again, periodically, to maintain the non-wrinkled appearance.

Similarly, filler materials are often used, for example, within a patient's lips, to expand their size in keeping with the desires of the patient. Such dermal fillers include those sold under the Trademarks Juvederm®, Restylane® and Radiesse®.

When such chemicals are injected, typically to reduce pain associated with such injections, two options are employed. A first option is the use of a topical numbing cream applied to the area where the injection will take place. Typically, topical numbing creams require 40 minutes to 1 hour with occlusion to successfully numb the skin to a sufficient degree to render the subsequent injections painless. The second technique involves the use of numbing medicines such as Lidocaine®. However, the use of numbing medicines such as Lidocaine® is less preferred because it also requires needle injection through the skin which is not only painful, but can also distort the surrounding area, thereby making determination of the amount of filler to be subsequently placed more difficult. Additionally, injection of Lidocaine® may dilute the particles of subsequently injected Botox® making it easier for the Botox® substance to travel to distant locations and paralyze muscles the patient did not want to have paralyzed.

Additional methods of pre-injection cooling of the skin and associated tissues are also employed. For example, plain ice or ice-packed devices may be placed onto the skin and held there for a short period of time to numb the skin. Use of ice or ice-packed devices is inefficient and initially painful for the patient. Such devices must be placed onto the skin and held there for a short time and then must be removed with one hand and moved away from the patient by passing to an assistant or using some other technique. When these techniques are employed, often the physician is holding the ice pack which causes the physician's hand to be cooled and reduces effectiveness of the use of that hand. When the physician is injecting cosmetic medicines, one hand is used to work the syringe and the other is used to tense the skin, that is, to move the skin away from the muscle or palpate a bony landmark to aid in locating the proper place to inject the medicine. Use of ice can be messy and cold water resulting from melting of the ice can drip over the area to be injected. Use of ice, whether exposed or packed, limits the effectiveness of the physician who needs to have both hands available for the injection as explained above.

Another way to cool the area of the injection is to use a device consisting of a hose attached to an air cooling machine that blows cold air at the face. One such device is known by the Trademark Smartcool®. Such devices are expensive and often the patient complains that, as the cold air is blown at the face, it takes their breath away as quickly moving air rushes by their nose. Additionally, the surface area cooled by a Smartcool® device is often significantly greater than necessary to numb an anticipated injection.

Each of these prior art techniques used preliminary to an injection in a sensitive area of a patient such as on the face has its problems as explained above. The present invention was developed, keeping these problems in mind, and in an effort to provide a new technique to prepare a sensitive area of the human body to receive a cosmetic injection while avoiding messiness, pain, inconvenience, and expense. It is with these thoughts in mind that the present invention was developed.

Applicant is aware of the following prior art references:

U.S. Pat. No. 3,605,742 to Tibbs teaches a painless injection device which includes means for spraying a cooling fluid onto an injection site to numb the area prior to injection. The Tibbs device is extremely cumbersome including a large housing enclosing a syringe as well as the numbing device. An additional problem with Tibbs is that the needle path is not visible until the mechanism latch is released to expose the syringe bottom and attached needle. The actual depth of penetration of the needle appears to be set by the action of a spring which is not a sufficiently precise enough structure to allow placement of substances such as Botox® medicament or subcutaneous fillers. Additionally, the Tibbs device is clumsy since it has one depressor mechanism to express the syringe from the housing using a spring device and then a further attachment to the plunger end to deliver the medicament into the tissues. This may lead to imprecise placement of either the needle tip location or the desired depth of medicament dispersal, or both.

U.S. Pat. No. 4,725,265 to Sairenji discloses a syringe having an attached cooling gas injection nozzle for injecting a cooling gas onto skin where an injection is to take place. The gas is a vapo-coolant and the device includes a retractable rigid nozzle that is spring activated and serves as a conduit for spraying the vapo-coolant. The spring activation of the Sairenji device requires a second hand to disengage the downward position of the nozzle. Furthermore, Sairenji discloses a chamber into which the desired medicament is filled for injection into the patient, rather than a pre-filled disposable syringe. The Sairenji device is not practical for use where multiple sequential injections in spaced locations are contemplated. This is because all of the actions necessary to cause dispensing of the vapo-coolant then the injection make the Sairenji device extremely cumbersome and complicated.

U.S. Pat. No. 5,236,419 to Seney discloses a syringe including a distal portion containing a freezable chemical designed to engage the surface of the skin where an injection is to take place to cool that portion of the skin. Seney also discloses that it is known in the prior art to spray ethyl chloride onto a location of the skin as a topical anesthetic. However, Seney fails to teach or suggest dispensing a topical anesthetic by a device attached to a disposable syringe in the manner contemplated by the present invention.

U.S. Pat. No. 6,312,412 to Saied et al. discloses an apparatus and method for painless intramuscular or subcutaneous injections. In the Saied et al. device, a numbing agent is injected subcutaneously using a needle. The present invention improves upon the Saied et al. device by providing a topical dispensing of a numbing agent so that the pain inflicted on the patient by injecting the numbing agent is completely eliminated.

U.S. Pat. No. 6,936,028 to Hommann et al. discloses a cooling device for an injection apparatus. The Hommann et al. device is somewhat similar to that of Seney as including a cooling element surrounding the location where the syringe will be inserted, which cooling element is placed on the skin to cool it and numb it prior to the injection.

The present invention improves upon the teachings of the prior art described above by providing a simple spraying mechanism for spraying a topical anesthetic onto the skin where an injection is to take place using a disposable and sometimes pre-filled syringe.

SUMMARY OF THE INVENTION

The present invention relates to a syringe-attached topical anesthetic dispenser. The present invention includes the following interrelated objects, aspects and features:

(1) In a first aspect, the present invention in its preferred intended use is intended to be releasably attachable to a pre-filled disposable syringe. Of course, if desired, the syringe may be initially empty and require filling prior to injection.

(2) A clip is provided that includes a first opening sized to receive the barrel of the syringe. That opening may be formed in a clip portion that is resilient and includes a longitudinally open slot allowing the syringe barrel to be inserted laterally into the opening. Alternatively, the syringe barrel may also be inserted into the opening of the clip portion longitudinally. In either case, it is preferred that the longitudinally extending opening in the clip portion has a width less than the diameter of the barrel of the syringe so that if the syringe is being attached to the clip portion through lateral movement, the flexibility of the clip portion allows the longitudinal opening to be temporarily enlarged until the largest diameter portion of the syringe barrel passes the opening, whereupon the resiliency of the clip portion causes it to spring back and retain the syringe barrel within its opening.

(3) In the preferred embodiment of the present invention, the clip includes a receptacle portion sized to closely receive a pre-filled cannister of a topical numbing agent such as, for example, ethyl chloride. Typically, the pre-filled cannister includes a generally cylindrical chamber portion receivable within the receptacle portion of the clip and a distal neck portion having an outlet that may be opened by piercing a disc-like closure, thereby allowing the contents of the cannister to be dispensed.

(4) A dispenser is attached to the distal neck portion of the cannister. The dispenser includes an elongated flexible tube attached to the distal neck portion of the cannister and surrounded by a rigid tube for at least a portion of its length. A pivotable lever carries a tube compressor including a pinching member extending through an opening in the rigid tube and spring biased to a position at which it pinches closed the elongated passageway through the flexible tube. The elongated actuating lever is spring biased to a position at which the flexible tube is pinched closed.

(5) Preferably, the flexible tube protrudes distally of the rigid tube and is made of a suitable material allowing the distal end of the flexible tube to be bent and configured to aim the topical anesthetic at a desired location on the skin of the user. If desired, a nozzle may be provided at the distal end of the flexible tube designed to cause the topical anesthetic to be sprayed in a desired spray pattern.

(6) The present invention is easily attached to a disposable syringe and may be easily removed therefrom when the disposable syringe is to be discarded. Since the inventive topical anesthetic dispenser never comes in contact with the patient and its design precludes contamination of the flexible tube and the cannister containing the topical anesthetic, the inventive device may be used multiple times with multiple syringes and, even, multiple patients. Of course, the device may be used solely with a single patient and discarded after such use.

As such, it is a first object of the present invention to provide a syringe-attached topical anesthetic dispenser.

It is a further object of the present invention to provide such a device in which a disposable syringe may have the dispenser attached thereto and easily removed therefrom when the syringe is to be discarded.

It is a still further object of the present invention to provide such a device in which a flexible tube dispenses a topical anesthetic and the flexible tube may be bent to aim the anesthetic at a desired location on the skin of a patient.

It is a yet further object of the present invention to provide such a device in which a tube compressor is employed to control dispensing of the topical anesthetic.

It is a yet further object of the present invention to provide such a device in which the tube compressor is biased to a position stopping flow of topical anesthetic and includes an actuating lever that may be pivoted to control flow of topical anesthetic.

These and other objects, aspects and features of the present invention will be better understood from the following detailed description of the preferred embodiment when read in conjunction with the appended drawing figures.

BRIEF DESCRIPTION OF THE DRAWINGS

FIG. 2 shows an enlarged side perspective view of the present invention from a similar perspective as that of FIG. 1, but with certain parts broken away to show details and other parts shown in cross-section to show details.

SPECIFIC DESCRIPTION OF THE PREFERRED EMBODIMENT

Figure 1:
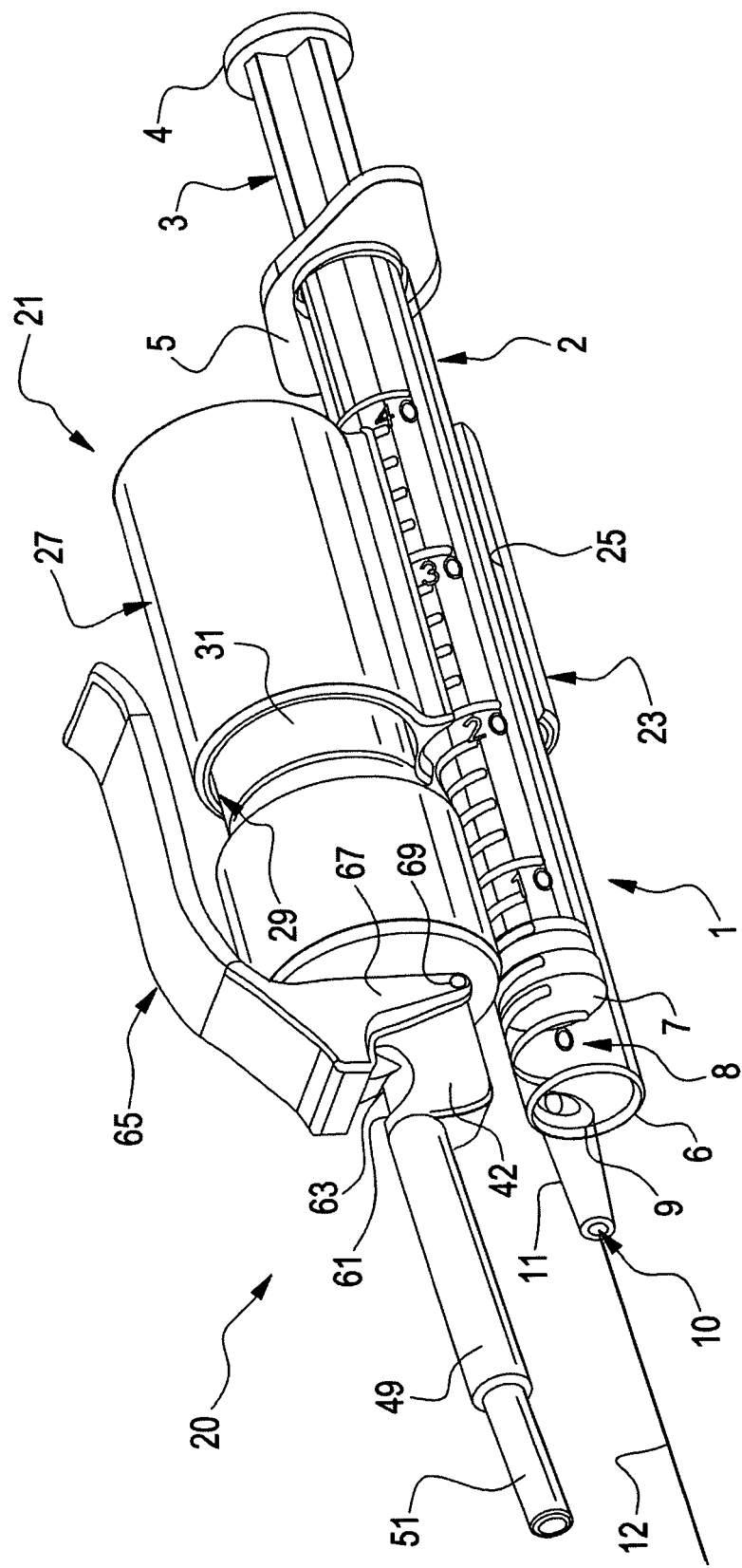
FIG. 1 shows a side perspective view of the present invention as attached to a disposable syringe.

Reference is first made to FIG. 1. As shown, a syringe 1 includes an elongated barrel 2 that is typically cylindrical in outer configuration, a plunger 3 having a proximal pad 4 that is engaged by a finger of the user, and a perpendicular tab 5 on the barrel 2 of the syringe 1 that is grasped by other fingers of the user while the pad 4 is being pushed to cause the plunger 3 to move in the distal direction toward the end 6 of the barrel 2.

The plunger 3 includes a piston 7 that pushes liquid in the chamber 8 through the outlet 9 in the chamber 8. A needle 12 is inserted into the opening 10 formed downstream of the outlet 9 in a tapered port 11. As is well known, the needle is thin and hollow permitting the medicament within the chamber 8 to be dispensed therethrough. The needle can be of any length so long as its distal end extends beyond the end of the tube 51 described below.

With reference to FIGS. 1 and 2, the present invention is generally designated by the reference numeral 20. The inventive dispenser 20 includes attachment means comprising a clip 21 having a clip portion 23 of arcuate construction and having a longitudinally elongated slot 25 having a width slightly smaller than the diameter of the barrel 2 of the syringe 1. The clip portion 23 is made of a flexible resilient material so that the width of the slot 25 may be temporarily enlarged by flexing it open, whereupon the barrel 2 of the syringe 1 may be inserted within the clip portion 23 and the flexing may be reversed causing the clip portion 23 to resiliently engage the outer periphery of the barrel 2 to retain the clip portion 23 assembled thereon.

The clip portion 23 also includes a receptacle or receptacle portion 27 including an internal chamber 29 defined by a closed end wall and a distal opening and is sized to receive a cannister 31 pre-filled with a topical anesthetic. The internal walls of the chamber 29 are sized and configured to snugly receive the cannister 31 while it being easy to remove the cannister 31 when it is desired to replace or replenish it. If desired, the internal walls of the chamber 29 may be roughened or provided with a lining such as of rubber or other sticky material to enhance the holding power of the chamber 29 for the cannister 31.

As best seen in FIG. 2, the cannister 31 includes a distal neck portion 33 having an outlet 35 that is initially closed, for example, by a piercable disc (not shown) that may suitably be pierced to allow the topical anesthetic contained within the cannister 31 to be dispensed.

With more particular reference to FIG. 2, the dispenser 20 also includes a housing 40 including a threaded recess 41. Preferably, the neck portion 33 of the cannister 31 has external threads and meshing with the threads 43 within the opening 41 to allow the cannister 31 to be releasably suitably fastened to the housing 40. The housing 40 includes a stepped cylindrical bore 45 with the step occurring at a shoulder 47. The distal portion of the bore 45 has an enlarged diameter and is sized to receive a rigid tube 49 which engages the shoulder 47 in assembled relation. The tube 49 may be secured to the housing 40 in any suitable manner such as through the use of an interference fit or adhesive. A flexible tube 51 is inserted into the rigid tube 49 and extends into the smaller diameter portion of the bore 45 as best seen in FIG. 2, surrounding the distal outlet 35 of the cannister 31.

The tube 51 has a distal end 53 having an opening 55 that may, if desired, be defined by a nozzle insert 57 inserted into the opening 55 and having a particularly configured passageway 59 to cause topical anesthetic sprayed therefrom to spray in a desired pattern. The distal end of the tube 51 is flexible and may be bent by a physician into a desired angulation so that the topical anesthetic is sprayed in a desired location with respect to the location where the syringe needle will be inserted beneath the skin of the patient. The needle 12 extends beyond the distal termination of the tube 51 so that the tube 51 doesn't interfere with insertion of the needle subcutaneously. The tube 51 has a proximal end 52 (FIG. 2) receiving the outlet 35 of the cannister 31.

The rigid tube 49 has an opening 61 (reference numeral shown in FIG. 1) through which a tube compressor 63 protrudes. As best seen in FIG. 1, the tube compressor 63 has an arcuate distal portion engaging the outer surface of the flexible tube 51 and is able to compress the tube 51 at that location to completely occlude the passageway 52 extending within the tube 51.

Valve means comprising a tube compressor 63 is integrally formed with a lever 65 pivotably mounted on the dispenser 40, the tube compressor 63 including an integrally formed arcuate shoulder (FIG. 1). In this regard, reference is made to FIG. 1 which shows the depending portion 67 of the lever 65 receiving a pin 69 extending through openings in the lever 65 (not shown) and an opening (not shown) through a portion 42 of the dispenser 40 so that the lever 65 pivots about the pin 69.

With reference to FIG. 2, the housing 40 includes a recess 44 that receives biasing means comprising a spring 71. The spring 71 has a proximal end engaging a proximal shoulder of the recess or blind bore 44 and a distal end engaging a shoulder 73 of the lever 65 so that the action of the compression spring 71 causes a force to be imposed in the left-hand direction in the view of FIG. 2 to cause the lever 65 to tend to pivot in a counterclockwise direction in the view of FIG. 2 about the pin 69 (FIG. 1). In this way, the tube compressor 63 is biased to the position shown in FIG. 2 at which it completely compresses the flexible tube 51 and completely occludes the passageway 52 to preclude any topical anesthetic from the cannister 61 from passing through the nozzle 57. The tube compressor valve may be used repeatedly as is well understood by those skilled in the art.

If desired, the proximal end of the flexible tube 51 may be provided with a hollow piercing element (not shown) designed to pierce a disc (not shown) on the distal outlet 35 of the cannister 31 when the cannister 31 neck 33 is being screwed into the threaded opening 41 of the dispenser 40 to open access to the cannister contents. In this way, once the cannister 31 is so installed, with the lever 65 biased to the position shown in FIG. 2, the anesthetic is ready to be dispensed, but will not be dispensed until the lever 65 is pivoted in the clockwise direction in the view of FIG. 2 to permit the tube compressor 63 to relieve pressure on the outer periphery of the flexible tube 51 and facilitate flow of anesthetic through the passageway 52 and out the nozzle 57 via the nozzle passageway 59.

With the present invention having been described in great detail hereinabove, its method of operation will now be explained. First, a syringe 1 is chosen and a desired needle 12 is installed into the port 10 thereof so that its distal end is distal of the nozzle 59 of the tube 51. The inventive dispenser 20 is attached to the barrel 2 of the syringe by expanding the longitudinal slot 25 in the clip portion 23, inserting the barrel 2 therewithin, and releasing the clip portion 23 to cause its inner surfaces to squeeze against the barrel 2 to retain it in appropriate position. In that position, the clip portion 23 may be slid along the barrel 2 to assume any desired location along the barrel length.

The location on the skin of the patient where an injection is to take place is determined and the syringe 1 with the dispenser 20 attached thereto is positioned at a desired location and angle of skin penetration approximately 1 to 2 centimeters above the skin. The lever 65 is depressed to pivot it about the pivot pin 69 to release the tube compressor 63 from the outer periphery of the flexible tube 51 to permit flow of the topical anesthetic such as ethyl chloride for a period of time, such as 1 to 3 seconds.

Either while the topical anesthetic is flowing or just after the flow of the topical anesthetic is stopped, the skin is then penetrated by the needle of the syringe 1 to a desired depth and, once the intramuscular location has been verified, the medicament is injected to the desired depth and amount. Injections may be subcutaneous, intramuscular or intradermal.

If desired, the needle may be retracted a desired distance with additional injection occurring or may be removed so that the next location can be chosen. During the process of injection including multiple injections at the same site of needle penetration, additional topical anesthetic may be dispensed as desired to maintain the numbness of the skin at that location.

If during the process of injection, the cannister 31 runs out of topical anesthetic, it may be removed from the receptacle 29 and replaced with a replacement cannister. The cannister 31 may also be refillable.

When the injection process is completed, the syringe 1 may be removed from the clip portion 23 and suitably discarded and the dispenser 20 may be re-used with other syringes.

As such, in this way, the present invention provides an effective way of dispensing a topical anesthetic such as ethyl chloride onto the skin of a patient where an injection is to take place so that the injection is painless. The present invention is not limited for use in association with injections in the face for aesthetic enhancement. Rather, it may be used as attached to any syringe or other injection device used to inject any medication for any purpose. For example, the inventive device may be used with injection devices associated with diabetes glucose monitors and multiple needle allergy introducers.

In the preferred embodiment of the present invention, the clip 27 is made of any suitable material such as molded plastic or light metal, although molded plastic is preferred. The housing 40 may be made of a molded plastic as may the lever 65 with its integral tube compressor 63. The tube 49 is made of any suitable rigid plastic while the tube 51 is made of any suitable flexible material allowing the distal end thereof to be bent to a desired angulation and to retain its bent orientation.

As such, an invention has been disclosed in terms of a preferred embodiment thereof which fulfills each and every one of the objects of the invention as set forth hereinabove, and provides a new and useful syringe-attached topical anesthetic dispenser of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A topical anesthetic dispenser, comprising:
   a) a receptacle sized to removably receive a cannister containing liquid anesthetic;
   b) attachment means on said receptacle for releasably attaching said receptacle to a syringe;
   c) said cannister having an outlet for dispensing said liquid anesthetic;
   d) a housing attached to said cannister, said housing including a tube with a passageway, said tube having a proximal end and an unpointed distal end, said proximal end being fluidly connected to said outlet of said cannister within said housing, and said distal end comprising a nozzle through which said liquid anesthetic sprays when dispensed from said cannister, said attachment means being integrally attached to said receptacle; and
   e) valve means engaging said tube for selectively and repeatedly controlling flow of said liquid anesthetic through said tube from said cannister to said nozzle, said liquid anesthetic being sprayed from said nozzle topically onto a skin surface.

2. The dispenser of claim 1, wherein said attachment means comprises a clip adapted to releasably attach around a barrel of said syringe.

3. The dispenser of claim 2, wherein said clip includes an arcuate wall and a longitudinally extending split.

4. The dispenser of claim 1, wherein said receptacle is generally cylindrical with a proximal closed wall and a distal opening.

5. The dispenser of claim 1, wherein said tube is flexible.

6. The dispenser of claim 5, wherein said nozzle comprises a nozzle insert inserted into said distal end of said tube, said nozzle insert including a fluid passageway therethrough.

7. The dispenser of claim 5, wherein said valve means comprises a tube compressor.

8. The dispenser of claim 7, wherein said tube compressor comprises a lever pivoted to said housing, said lever including a shoulder squeezing said tube closed in a first position and releasing said tube in a second position.

9. The dispenser of claim 8, further including biasing means for biasing said lever toward said first position of said shoulder.

10. The dispenser of claim 9, wherein said biasing means comprises a compression spring.

11. The dispenser of claim 10, wherein said spring is received in a blind bore in said housing, one end of said spring engaging a closed end of said blind bore and another end of said spring engaging said lever.

12. The dispenser of claim 8, wherein said lever is pivoted at a pivot located between said tube and said attachment means.

13. The dispenser of claim 12, wherein said attachment means comprises a clip adapted to releasably attach around a barrel of said syringe.

14. The dispenser of claim 1, wherein said syringe includes a needle having a distal tip, said distal tip being distal of said distal end of said tube.

15. The dispenser of claim 14, wherein said valve means comprises a tube compressor.

16. The dispenser of claim 15, wherein said tube compressor comprises a lever pivoted to said housing, said lever including a shoulder squeezing said tube closed in a first position and releasing said tube in a second position.

17. A topical anesthetic dispenser, comprising:
   a) a cylindrical receptacle sized to removably receive a cannister containing liquid anesthetic;
   b) attachment means comprising a clip included with said receptacle for releasably attaching around a barrel of a syringe, said clip including an arcuate wall and a longitudinally extending split;
   c) said cannister having an outlet for dispensing said liquid anesthetic;
   d) a housing attached to said cannister, said housing including a flexible tube having a proximal end and an unpointed distal end, said proximal end being fluidly connected to said outlet of said cannister within said housing and said distal end comprising a nozzle through which said liquid anesthetic flows when dispensed from said cannister; and
   e) a tube compressor associated with said housing for selectively and repeatedly controlling flow of said liquid anesthetic from said cannister to said nozzle by squeezing or releasing said tube, said liquid anesthetic being sprayed from said nozzle topically onto a skin surface.

18. The dispenser of claim 17, wherein said tube compressor comprises a lever pivoted to said housing, said lever including a shoulder squeezing said tube closed in a first position and releasing said tube in a second position.

19. The dispenser of claim 18, further including a compression spring biasing said lever toward said first position of said shoulder.

20. The dispenser of claim 17, wherein said syringe includes a needle having a distal tip, said distal tip being distal of said distal end of said tube.

* * * * *